United States Patent
Lang et al.

(10) Patent No.: US 9,975,103 B2
(45) Date of Patent: May 22, 2018

(54) PROCESS AND APPARATUS FOR PREPARATION OF POLYSILANES

(71) Applicants: Juergen Erwin Lang, Karlsruhe (DE); Hartwig Rauleder, Rheinfelden (DE); Ekkehard Mueh, Rheinfelden (DE)

(72) Inventors: Juergen Erwin Lang, Karlsruhe (DE); Hartwig Rauleder, Rheinfelden (DE); Ekkehard Mueh, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 234 days.

(21) Appl. No.: 14/782,099

(22) PCT Filed: Feb. 28, 2014

(86) PCT No.: PCT/EP2014/053943
§ 371 (c)(1),
(2) Date: Oct. 2, 2015

(87) PCT Pub. No.: WO2014/173569
PCT Pub. Date: Oct. 30, 2014

(65) Prior Publication Data
US 2016/0030911 A1 Feb. 4, 2016

(30) Foreign Application Priority Data

Apr. 24, 2013 (DE) .......... 10 2013 207 443

(51) Int. Cl.
*B01J 19/08* (2006.01)
*C01B 33/04* (2006.01)
*C07F 7/08* (2006.01)

(52) U.S. Cl.
CPC ............. *B01J 19/088* (2013.01); *C01B 33/04* (2013.01); *C07F 7/0801* (2013.01); *C07F 7/0805* (2013.01); *B01J 2219/00038* (2013.01); *B01J 2219/0805* (2013.01); *B01J 2219/0847* (2013.01); *B01J 2219/0849* (2013.01); *B01J 2219/0883* (2013.01); *Y02P 20/582* (2015.11)

(58) Field of Classification Search
CPC .................................................. Y02P 20/2582
See application file for complete search history.

(56) References Cited

U.S. PATENT DOCUMENTS 4,604,274 A   8/1986   Zavelovich et al.
4,941,893 A *   7/1990   Hsieh ..................... B01D 53/22
                                          423/342

(Continued)

FOREIGN PATENT DOCUMENTS

EP    0 268 756 A2   6/1988
FR    2 743 554 A1   7/1997

(Continued)

OTHER PUBLICATIONS

International Search Report dated Jun. 18, 2014, in PCT/EP2014/053943 filed Feb. 28, 2014.

(Continued)

*Primary Examiner* — Kishor Mayekar
(74) *Attorney, Agent, or Firm* — Oblon, McClelland, Maier & Neustadt, L.L.P.

(57) ABSTRACT

The invention relates to a process for preparing polysilanes by converting monosilane in the presence of hydrogen in a plasma, and to a plant for performing the process.

16 Claims, 2 Drawing Sheets

(56) References Cited

U.S. PATENT DOCUMENTS

| | | | |
|---|---|---|---|
| 4,950,373 A * | 8/1990 | Sundermeyer | B01J 12/002 204/164 |
| 5,478,453 A | 12/1995 | Bernard et al. | |
| 5,505,913 A | 4/1996 | Bernard et al. | |
| 2011/0206591 A1 * | 8/2011 | Laine | C01B 33/023 423/349 |
| 2013/0043893 A1 | 2/2013 | Mueh et al. | |
| 2014/0178284 A1 | 6/2014 | Lang et al. | |

FOREIGN PATENT DOCUMENTS

| WO | WO 2011/103941 A1 | 9/2011 |
|---|---|---|
| WO | WO 2013/007426 A1 | 1/2013 |
| WO | WO 2014/173566 A1 | 10/2014 |
| WO | WO 2014/173567 A1 | 10/2014 |
| WO | WO 2014/173573 A1 | 10/2014 |
| WO | WO 2014/173574 A1 | 10/2014 |

OTHER PUBLICATIONS

U.S. Appl. No. 14/782,247, filed Oct. 2, 2015, Lang et al.
U.S. Appl. No. 14/782,545, filed Oct. 5, 2015, Lang et al.
U.S. Appl. No. 14/782,433, filed Oct. 5, 2015, Lang et al.
U.S. Appl. No. 14/782,470, filed Oct. 5, 2015, Lang et al.

\* cited by examiner

PROCESS AND APPARATUS FOR PREPARATION OF POLYSILANES

The invention relates to a process for preparing polysilanes by converting monosilane in the presence of hydrogen in a plasma, and to a plant for performing this process.

BACKGROUND

In microelectronics, disilane is used for deposition of silicon layers, and this has to meet ultrahigh purity demands. However, the only processes known to date use catalysts. For instance, JP 02-184513 discloses a process for preparing disilane using organometallic catalysts based on platinum, rhodium or ruthenium complex catalysts having organic phosphorus, arsenic or antimony ligands. These catalysts contribute to contamination in the ppb range of the disilane prepared and the disposal thereof is being viewed increasingly critically.

WO 2008/098640 A2 discloses a process for preparing hexachlorodisilane, which can be hydrogenated catalytically to disilane in a second process step. This two-stage process is unsuitable for the inexpensive preparation of high-purity disilane.

DE 36 39 202 discloses a further process for preparing disilane having the disadvantage of formation of significant amounts of elemental silicon during the preparation of disilane. The reactor can only be operated batchwise in this process and has to be cleaned in a costly and inconvenient manner after very short production times. A further disadvantage lies in the high yield losses which arise firstly through the silicon deposition and secondly through losses of disilane or trisilane because of stripping effects in the removal of hydrogen from the reaction products. These yield losses can be avoided in the case of synthesis via hexachlorodisilane, but the catalytic hydrogenation in turn results in contamination of the disilane and trisilane. The problem addressed by the present invention was that of providing a process and a plant which avoids the disadvantages of the prior art mentioned and preferably allows a continuous preparation of polysilanes. In addition, it was to be possible to isolate the polysilanes, even as a mixture, in high to ultrahigh purity. Preferably, a separation of the polysilanes was merely to serve the purpose of increasing the content of the pure polysilanes and not for the primary purpose of purification. An additional problem was that of providing a particularly economically viable process on the industrial scale.

These problems are solved by the process according to the invention and by the plant according to the invention.

It has been found that, surprisingly, for selective preparation of polysilanes, it is possible to utilize gas phase treatments of a stream of reactants comprising monosilane with a defined partial monosilane pressure in the gas mixture in the presence of hydrogen in nonthermal plasmas at temperatures below 40° C. and preferably reduced pressure.

SUMMARY

The invention thus provides a process for preparing polysilanes having at least two silicon atoms bonded to one another via a covalent single bond (Si—Si), especially mixtures of linear, branched and/or cyclic polysilanes selected from disilane, trisilane, tetrasilane, pentasilane, hexasilane, heptasilane, octasilane, nonasilane, decasilane, undecasilane, dodecasilane and/or structural isomers thereof, preferably polysilanes of the general formulae II, III, IV and/or V below, by i) subjecting a stream of reactants comprising monosilane of the general formula I and hydrogen, especially a stream of reactants in a gas mixture,

ii) to at least one gas discharge, preferably two to ten nonthermal plasmas, preferably at a pressure between 0.05 $mbar_{abs.}$ to 15 000 $mbar_{abs.}$, more preferably under reduced pressure, and iii) setting a defined ratio of the partial hydrogen pressure to the partial pressure of the silanes which are gaseous under the conditions selected in the resulting phase, and likewise in step iii) obtaining polysilanes from the resulting phase, especially polysilane mixtures, preferably linear, branched and/or cyclic polysilanes having 2 to 25 silicon atoms, preferably having 4 to 25 silicon atoms, such as tetrasilane, pentasilane, hexasilane, heptasilane, octasilane, nonasilane, decasilane, undecasilane, dodecasilane and/or structural isomers thereof, it being particularly preferable when, in step iii,) first the polysilanes are obtained and then a defined ratio of the partial hydrogen pressure to the partial pressure of the silanes which are gaseous under the conditions selected, especially of the monosilane and optionally of the disilane, is set in the resulting phase, and then iv) the polysilane mixture is separated, more particularly separated by means of distillation, fractional condensation and/or by chromatography. More preferably, the polysilane mixture is separated into the individual polysilanes by means of fractional distillation in a multicolumn system. In the context of the invention, the term "silane" covers both monosilane and the polysilanes, while "polysilane" is considered to be only silanes having at least two silicon atoms, preferably having at least four silicon atoms.

According to the invention, the setting of the partial pressures is accomplished by means of a hydrogen-permeable membrane which is preferably permeable only to hydrogen and is essentially impermeable to silanes. Alternatively, it is likewise especially preferable when, in step iii), the polysilanes are obtained simultaneously in the resulting phase and a defined ratio of the partial hydrogen pressure to the partial pressure of the silanes which are gaseous under the conditions selected is set.

DETAILED DESCRIPTION

Figure 1:
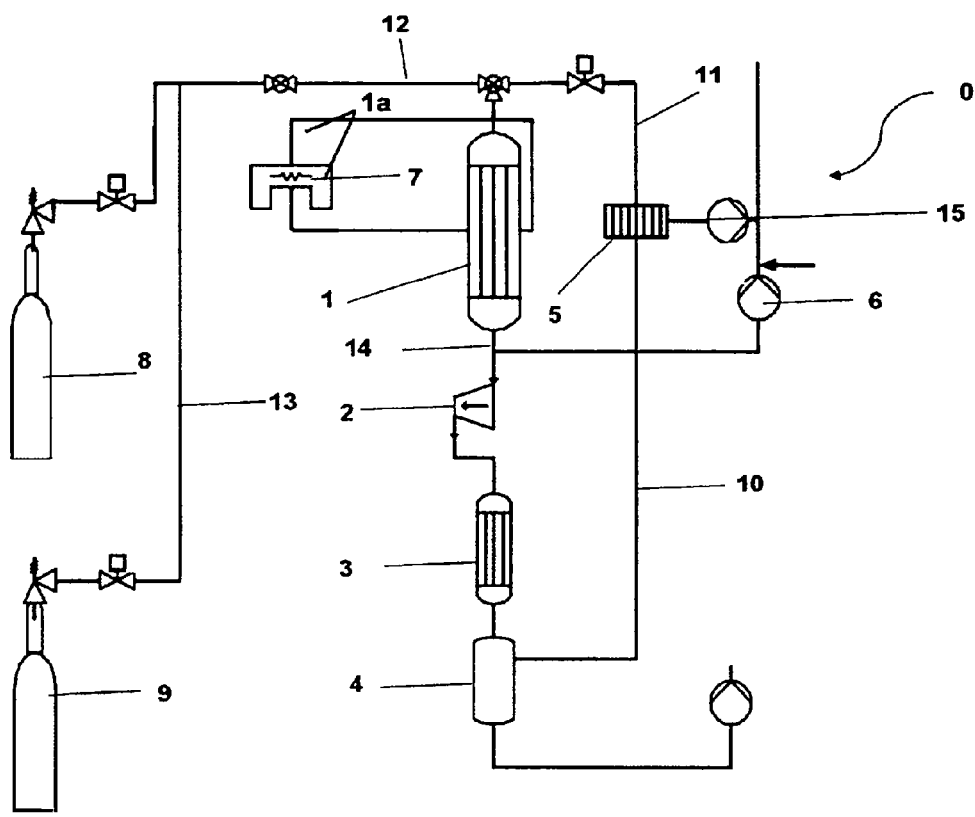
FIG. 1 shows a schematic diagram of a plant 0 for performance of a cycle process.

The term "polysilane" encompasses the homologous series of the purely hydrogen-substituted silanes according to IUPAC nomenclature, which, as inventive polysilanes, have at least two silicon atoms covalently bonded to one another (Si—Si). The polysilanes have a silicon base skeleton substituted exclusively by hydrogen atoms and include linear, branched and/or cyclic polysilanes, such as n-polysilanes, isopolysilanes, neopolysilanes and/or cyclopolysilanes. The linear and branched polysilanes can be described by the general formula II $Si_nCl_{2n+2}$ where n is greater than or equal to 2, and the cyclic polysilanes by the general formula III $Si_nCl_{2n}$ where n is greater than or equal to 3. In an idealized manner, high molecular weight polysilanes can be described by the formula IV $Si_nCl_{2n}$ where n is greater than or equal to 3, or else by the formula V with a further-reduced hydrogen component $((SiH_{<2})_n)$. Polysilanes according to the invention are understood to mean both individual polysilanes and mixtures of polysilanes of the general formulae II, III, IV and/or V where n is greater than or equal to 2 to 100, especially where n is greater than or equal to 2 to 25, preferably where n is 4 to 25, more preferably where n is 4 to 15, the polysilanes preferably being liquid to highly viscous under the process conditions. Therefore, the polysilanes in accordance with the invention preferably include mixtures of high-to ultrahigh-purity silanes selected from disilane, trisilane, tetrasilane, pentasilane, hexasilane, heptasilane, octasilane, nonasilane, decasilane, undecasilane, dodecasilane, tridecasilane, tetradecasilane, pentadecasilane, cyclopentasilane, cyclohexasilane, and the structural isomers and high molecular weight polysilanes of each up to preferably n less than or equal to 25, the polysilane comprising at least tetrasilane and/or pentasilane.

A particular advantage of the process according to the invention is the possibility of direct further processing of the polysilanes for deposition of high-purity silicon layers with solar silicon quality or else semiconductor quality without additional purification steps. There is merely a separation of the polysilane mixture into the individual polysilanes by means of distillative workup, in order to ensure defined product properties of the polysilanes in the further processing. According to the invention, these polysilanes are essentially free of halogens, especially essentially chlorine-free, the chlorine content thereof preferably being below $1 \times 10^{-5}\%$ by weight, more preferably below $1 \times 10^{-6}\%$ by weight down to the detection limit of $1 \times 10^{-10}\%$ by weight. The polysilanes obtainable in accordance with the invention are thus free of halogen, such as chlorine.

The invention thus provides a process for preparing polysilanes and polysilane mixtures, i) wherein a stream of reactants comprising monosilane of the general formula I and hydrogen in the gas mixture ii) is exposed to nonthermal plasmas at a pressure between 0.1 $mbar_{abs.}$ and 1000 $mbar_{abs.}$, preferably at a pressure between 1 $mbar_{abs.}$ and 950 $mbar_{abs.}$, and iii) a ratio of the partial hydrogen pressure to the partial pressure of the silanes which are gaseous under the selected conditions, especially to the partial pressure of the monosilane, is set in the resulting phase, and polysilane mixtures are obtained, where the pressure in process step iii) is elevated relative to the pressure in process stage ii), and iv) the polysilane mixture is distilled.

The reactants used are high- to ultrahigh-purity monosilane and hydrogen which preferably each correspond to the impurity profile which follows. The total contamination in the monosilane or the hydrogen is less than or equal to 100 ppm by weight to 1 ppt by weight, especially to the detection limit, preferably less than or equal to 50 ppm by weight, further preferably less than or equal to 25 ppm by weight. The total contamination includes contamination with boron, phosphorus and metallic elements other than silicon. More preferably, the total contamination, in each case independently, for the monosilane and the hydrogen is, for the following elements, less than or equal to:

aluminium from 15 ppm by weight to 0.0001 ppt by weight, and/or
a. boron from 5 to 0.0001 ppt by weight, preferably in the range from 3 ppm by weight to 0.0001 ppt by weight, and/or
b. calcium from 2 ppm by weight to 0.0001 ppt by weight, and/or
c. iron from 5 ppm by weight to 0.0001 ppt by weight, preferably from 0.6 ppm by weight to 0.0001 ppt by weight, and/or
d. nickel from 5 ppm by weight to 0.0001 ppt by weight, preferably from 0.5 ppm by weight to 0.0001 ppt by weight, and/or
e. phosphorus from 5 ppm by weight to 0.0001 ppt by weight, preferably from 3 ppm by weight to 0.0001 ppt by weight, and/or
f. titanium less than or equal to 10 ppm by weight, preferably less than or equal to 2 ppm by weight, further preferably from 1 ppm by weight to 0.0001 ppt by weight, more preferably from 0.6 ppm by weight to 0.0001 ppt by weight, most preferably from 0.1 ppm by weight to 0.0001 ppt by weight, and/or
g. zinc less than or equal to 3 ppm by weight, preferably from 1 ppm by weight to 0.0001 ppt by weight, more preferably from 0.3 ppm by weight to 0.0001 ppt by weight,
h. carbon and/or
i halogens, where the concentrations i and j are each in the region of the detection limit of the respective measurement method known to those skilled in the art.

It has been found that, for a given stream of reactants having a ratio of hydrogen and silane, in each case in percent by volume ( % by vol.) of preferably 15:1 to 1:5, preferably between 10:1 and 5:1, more preferably between 10:1 and 8:1, further preferably with about 90% by vol. of hydrogen and 10% by vol. of monosilane, i.e. at a ratio of about 9:1, the best yields of polysilanes are obtained when the pressure in the gas discharge reactor is between 10 and 60 $mbar_{abs.}$.

Thus, for a stream of reactants of 90% by vol. of hydrogen and 10% by vol. of monosilane, after flowing through two gas discharge arrangements of nonthermal plasmas at a pressure of 10 $mbar_{abs.}$, polysilane can be obtained in a continuous mode of operation. If the pressure is further increased slightly, the yield can be enhanced further.

In a particularly preferred process regime, the stream of reactants in process step ii) is exposed to two to ten gas discharges. Generally, it may be preferable when the stream of reactants flows through several gas discharge arrangements of nonthermal plasmas, especially 2, 3, 4, 5, 6, 7, 8, 9 or 10 nonthermal plasmas, preference being given to 2 to 4 plasmas. According to the desired molecular weight distribution of the polysilanes, the stream of reactants is contacted with a greater number or smaller number of nonthermal plasmas. For preparation of polysilanes having high molecular weight, the stream of reactants is contacted with a plurality of nonthermal plasmas connected in series.

For optimal performance of the process, the stream of reactants is preferably subjected to nonthermal plasmas in step ii) at a pressure of 5 $mbar_{abs.}$ to 100 $bar_{abs.}$, more preferably of 7.5 $mbar_{abs.}$ to 100 $mbar_{abs.}$, further preferably of 10 $mbar_{abs.}$ to 80 $mbar_{abs.}$, within a temperature range from −60° C. to 10° C., preferably −40 to 0° C., further preferably around −10° C. plus/minus 5° C.

It is likewise preferred when the gas discharge in process step ii) is effected at
a pressure between 0.1 mbar$_{abs.}$ and 1000 mbar$_{abs.}$,
preferably of 0.1 to 800 mbar$_{abs.}$,
more preferably of 1 mbar$_{abs.}$ to 100 mbar$_{abs.}$.
Further preferred is a
pressure range from 10 to 100 mbar$_{abs.}$,
preferably from 10 to 80 mbar$_{abs.}$.

It is further preferable when the gas discharges, especially the nonthermal plasmas, are operated in step ii) within a temperature range from −60° C. to 10° C.

For preparation of the polysilanes, the reaction conditions in the nonthermal plasmas are adjusted selectively to the excitation and scission of the Si—H bond or of Si—Si bonds. Within the preferred pressure and temperature ranges, the nonthermal plasma can selectively excite the Si—H bond and/or the Si—Si bonds to such an extent that there is selective free-radical formation and subsequent recombination with other free radicals. Under the process conditions selected, preferably silyl radicals (SiH$_3$ radicals), SiH$_2$ radicals and corresponding radicals of the polysilanes formed are formed. Through recombination and chain growth of the aforementioned radicals, branched polysilanes can be obtained.

It is suspected that, at a mean electron energy of 5 eV in the weakly ionizing nonthermal plasma, there is selective formation of silyl radicals through excitation and scission of the Si—H bond. For further chain extension, an insertion of SiH$_2$ radicals into Si—H or Si—Si bonds of disilanes, trisilane, tetrasilane and higher silanes probably takes place. If the energy input is too high, for example in the region of 12.3 eV, unwanted SiH$_3^+$ ions would be formed rather than selective free-radical formation. These ions would decompose and lead to deposition of silicon. For a high polysilane yield, it is therefore crucial to optimize the process conditions in the nonthermal plasmas for selective radical formation and the possibilities of recombination to polysilanes, and at the same time to suppress the formation of further decomposition products. This is possible with optimal matching of pressure and energy input to one another.

The polysilane mixture formed can subsequently be condensed out via a suitable temperature and pressure setting, especially after step III), by adjusting the pressure by means of a compressor to a pressure of 0.1 bar$_{abs.}$ to 100 bar$_{abs.}$, especially of 1 bar$_{abs.}$ to 100 bar$_{abs.}$, preferably of 1 to 10 bar$_{abs.}$, and within a temperature range from −60° C. to 20° C. For complete removal, preference is given to employing a two-stage procedure in which, in a first component step, a temperature in the range from −20 to 300° C. is established in the condenser at a pressure between 0.1 and 10 bar$_{abs.}$, and subsequently the complete removal is effected in the crude product vessel or crude product outlet at preferably the same pressure at −20 to 40° C. by condensation of the polysilanes out of the resulting phase.

This resulting phase is preferably contacted with a membrane permeable to hydrogen, in which case a defined ratio of the partial hydrogen pressure to the partial pressure of the silanes which are gaseous under the conditions selected, especially of the unconverted monosilane, can be established. The resulting phase which has been treated in this way, after the partial removal of hydrogen, becomes the stream of reactants again, into which further monosilane can be metered before it is sent to the nonthermal plasma.

In the process according to the invention, linear, branched and/or cyclic polysilanes comprising tetrasilane, pentasilane and/or hexasilane are obtained, which are preferably already obtained in high or ultrahigh purity according to the definition below, as the polysilane mixture. By means of distillation, the polysilanes can be separated into the individual polysilanes in a simple manner.

The aforementioned procedure allows the simple recycling of unconverted reactant of the general formula I, which, if required, can be sent back to the nonthermal plasma. For complete conversion of the monosilane used to polysilanes, preferably two to five nonthermal plasmas are run through in step ii), and the process can additionally be operated as a cycle process by running through process steps i), ii) and iii). The polysilane obtained by means of the conversion in the nonthermal plasma can already be obtained in pure form directly via process steps i, ii) and iii). A separation and any additional further purification of the silanes can subsequently be effected by continuous or batchwise distillation. According to the product mixture obtained, the distillative workup can be effected with one column or preferably in a multicolumn system, when different polysilanes are to be separated.

The process according to the invention gives pentasilane, which can be isolated in ultrahigh purity from the other polysilanes. In a $^{29}$Si NMR spectrum, aside from the signal for pentasilane, no further products are detectable. The contamination of the polysilane, especially of the pentasilane, with other metal compounds is within the range from 1000 ppb by weight to 100 ppt by weight, preferably less. A particular advantage of the polysilanes prepared by the process according to the invention is that they are free of chlorides and/or catalyst residues otherwise typically used.

More preferably, the polysilane obtained and the respectively isolated individual polysilanes are of ultrahigh purity and in each case has a sum total of total contamination of less than or equal to 100 ppm by weight down to the detection limit, especially to 1 ppt by weight, the total contamination preferably being less than or equal to 50 ppm by weight. The total contamination is regarded as being contamination with boron, phosphorus and metallic elements other than silicon. More preferably, the total contamination of the polysilane for the following elements is less than or equal to:

aa. aluminium from 15 ppm by weight to 0.0001 ppt by weight, and/or bb. boron from 5 to 0.0001 ppt by weight, preferably in the range from 3 ppm by weight to 0.0001 ppt by weight, and/or cc. calcium less than 2 ppm by weight, preferably from 2 ppm by weight to 0.0001 ppt by weight, and/or dd. iron from 5 ppm by weight to 0.0001 ppt by weight, preferably from 0.6 ppm by weight to 0.0001 ppt by weight, and/or ee. nickel from 5 ppm by weight to 0.0001 ppt by weight, preferably from 0.5 ppm by weight to 0.0001 ppt by weight, and/or ff. phosphorus from 5 ppm by weight to 0.0001 ppt by weight, preferably from 3 ppm by weight to 0.0001 ppt by weight, and/or gg. titanium less than or equal to 10 ppm by weight, less than or equal to 2 ppm by weight, preferably from 1 ppm by weight to 0.0001 ppt by weight, further preferably from 0.6 ppm by weight to 0.0001 ppt by weight, especially preferably from 0.1 ppm by weight to 0.0001 ppt by weight, and/or hh. zinc less than or equal to 3 ppm by weight, preferably from 1 ppm by weight to 0.0001 ppt by weight, further preferably from 0.3 ppm by weight to 0.0001 ppt by weight,
ii. carbon, and/or
jj. halogens, preference being given to a purity for each element aa to jj in the region of the detection limit for the measurement method known to those skilled in the art. The total contamination with the aforementioned elements is preferably determined by means of ICP-MS. Overall, the process can be monitored continuously by means of online analysis. The required purity can be checked by means of GC, IR, NMR, ICP-MS, or by resistance measurement or GC-MS after deposition of the Si.

Additionally or alternatively to one of the aforementioned features, it is preferable to set the resulting phase in process step iii) to a pressure of 0.05 $bar_{abs.}$ to 100 $bar_{abs.}$, for example to 0.1 to 100 $bar_{abs.}$, preferably to a pressure of 1 $bar_{abs.}$ to 100 $bar_{abs.}$, further preferably to a pressure of 0.5 $bar_{abs.}$, more preferably to 1 $bar_{abs.}$, to 60 $bar_{abs.}$. Particular preference is given to a pressure of 1 to 10 $bar_{abs.}$.

The hydrogen-permeable membrane used in the process and/or in the plant may preferably be a membrane comprising the following materials: quartz, suitable metal, suitable metallic alloy, ceramic, zeolite, organic polymer and/or a composite membrane comprising an at least two-layer structure with one or more of the aforementioned materials. In order to be suitable as material for the hydrogen-permeable membrane, it is necessary that the material, for example quartz or palladium, with or without silver, has pores of a defined size through which hydrogen can diffuse and which are essentially impermeable to monosilane. A membrane used with preference may comprise, for example, a ceramic membrane having a layer structure having a first microporous layer with pores smaller than 2 nm, adjoined by a mesoporous layer having pores of 3 to 10 nm. Preferably, a macroporous layer having large pores up to 100 nm may be provided. It is preferable in this case when the macroporous layer is a porous ceramic material or a sintered metal.

Suitable membranes may preferably include the following materials: palladium, a palladium alloy such as PdAl, PdCu, quartz and/or an organic synthetic polymer, such as preferably hollow fibre membranes, the membranes preferably being permeable to hydrogen. Preferred hollow fibre membranes may be produced from polyamides, polyimides, polyamideimides or else from mixtures of these. If a palladium membrane is selected, it can be produced, for example, by chemical gas phase deposition, electrochemical deposition, high-velocity flame spraying or physical gas phase deposition, what is called electron beam vaporization or what is called sputtering.

Because of the high purity demands in relation to contamination with metallic elements, preference is given to utilizing an ultrahigh-purity quartz membrane in the process and/or in the plant. This membrane should have a pressure stability greater than 1 $bar_{abs.}$, preferably greater than 2 $bar_{abs.}$, more preferably greater than 3 $bar_{abs.}$, and may preferably be applied to a porous Si support or alumina support. The same applies to palladium-based membranes, which can be produced from a palladium-aluminium, palladium-silver or palladium-copper alloy and preferably have a pressure stability greater than 3 $bar_{abs.}$, on a porous Si support, a so-called perforated mask support or an aluminium oxide support.

Every nonthermal plasma is based on anisothermal plasma. It is generated in a plasma reactor in which a plasmatic conversion of matter is induced. Characteristic features of these plasmas are a high electron temperature $T_e > 10^4$ K and relatively low gas temperature $T_G \approx 10^3$ K. The activation energy needed for chemical processes is exerted predominantly through electron impacts. Typical nonthermal plasmas can be generated, for example, by glow discharge, HF discharge, hollow cathode discharge or corona discharge. The working pressure at which the inventive plasma treatment is performed is preferably in the range from 1 to 1000 $mbar_{abs.}$, the phase to be treated preferably being set to a temperature of −40° C. to 10° C. For a definition of nonthermal plasma and of homogeneous plasma catalysis, reference is made to the relevant technical literature, for example to "Plasmatechnik: Grundlagen and Anwendungen—Eine Einfuhrung [Plasma Technology: Fundamentals and Applications—An Introduction]; collective of authors, Carl Hanser Verlag, Munich/Vienna; 1984, ISBN 3-446-13627-4".

The invention likewise provides a plant, especially for performance of the aforementioned process, having an apparatus which comprises at least two reactors, especially two series-connected reactors, for generation of gas discharges and has a dedicated upstream reactant feed and a dedicated downstream hydrogen-permeable membrane, in order to set a defined ratio of the partial hydrogen pressure to the partial pressure of the gaseous silanes in the resulting phase, the plant further having at least one further apparatus for separation of the polysilanes, the further apparatus preferably being a column for distillative workup of the polysilanes. The plant preferably has a multicolumn system having at least 2 columns, preferably having 2 to 5 columns.

In addition to the two reactors, the plant may also have one or more further reactors connected in series and/or in parallel. Preferably, 2, 3, 4, 5, 6, 7, 8, 9 or 10 reactors may be connected in series. According to the invention, the reactors are preferably ozonizers. A great advantage lies in the alternative possible use of commercial ozonizers, such that the capital costs can be lowered significantly. The reactors of the invention are appropriately equipped with glass tubes, especially with quartz glass tubes, the tubes preferably being arranged in parallel or coaxially and being spaced apart by means of inert material spacers. Suitable inert materials are especially Teflon, glass, and generally low-K materials having a low dielectric constant. Materials having a low dielectric constant are considered to be those whose dielectric constant is less than or equal to 9. Alternatively, the reactors may be equipped with tubular, dielectric components rather than with glass tubes. It is known that the electron energy injected for the plasma discharge "E" is dependent on the product of pressure "p" and electrode spacing "d" (p·d). For the process according to the invention, the product of electrode spacing and pressure is generally in the range from 0.001 to 300 mm·bar, preferably from 0.05 to 100 mm·bar, more preferably 0.08 to 0.3 mm·bar, especially 0.1 to 0.2 mm·bar. The discharge can be induced by means of various kinds of AC voltages or pulsed voltages from 1 to $10^6$ V. The curve profile of this voltage may include rectangular, trapezoidal or pulsed profiles, or profiles composed piece by piece of individual profiles over time. Particularly suitable types are pulsed excitation voltages, which enable simultaneous formation of the discharge over the entire discharge space of the reactor. The pulse duration in pulsed operation is guided by the composition, the residence time and the pressure of the stream of reactants. It is preferably between 10 ns and 1 ms. Preferred voltage amplitudes are 10 Vp to 100 kVp, preferably 100 Vp to 10 Vp, especially 50 to 5 Vp, in a microsystem. The frequency of the AC voltage may be between 10 MHz and 10 ns pulses (duty ratio 10:1) down to low frequencies in the range from 10 to 0.01 Hz. For example, an AC voltage having a frequency of 1.9 kHz and an amplitude of 35 kV peak-to-peak can be applied in the reactor. The power input is about 40 W.

The invention likewise provides a preferred plant 0 as illustrated in FIG. 1, which, downstream of the apparatus 1 having at least two reactors 1a, has a dedicated compressor 2 to increase the pressure of the resulting phase, the compressor 2 more particularly being provided between the apparatus 1 and the membrane 5. The compressor increases the pressure of the resulting phase after it leaves the reactor, for example from about 60 $mbar_{abs.}$ to 2.5 $bar_{abs.}$. The compressed resulting phase is subsequently passed through a downstream condenser 3, in order to condense the polysilane formed, while unconverted monosilane and any disilane or further silanes which are gaseous under the conditions and hydrogen remain in the gas phase.

Thus, a particularly preferred plant 0 according to FIG. 1 has a compressor 2 downstream of the apparatus 1 having at least two reactors 1a, with a condenser 3 dedicated to said compressor 2 and a crude product outlet 4 or crude product vessel 4 dedicated to said condenser 3. Further provided downstream of the condenser 3, especially at or beyond the product vessel 4, is the membrane 5 for setting the partial hydrogen pressure of the resulting phase. The resulting phase is contacted with the membrane 5 and then a stream of reactants is obtained, which is transferred into the apparatus by means of a dedicated line 11 upstream of the apparatus 1. It is possible to meter further monosilane from the monosilane source 9 into this stream of reactants, in order either to adjust the content of monosilane in % by volume or else to regulate the pressure of the stream of reactants. A vacuum pump 6 dedicated to the reactor can be utilized for startup of the process and for regulation of the pressure during the running reaction.

Figure 2:
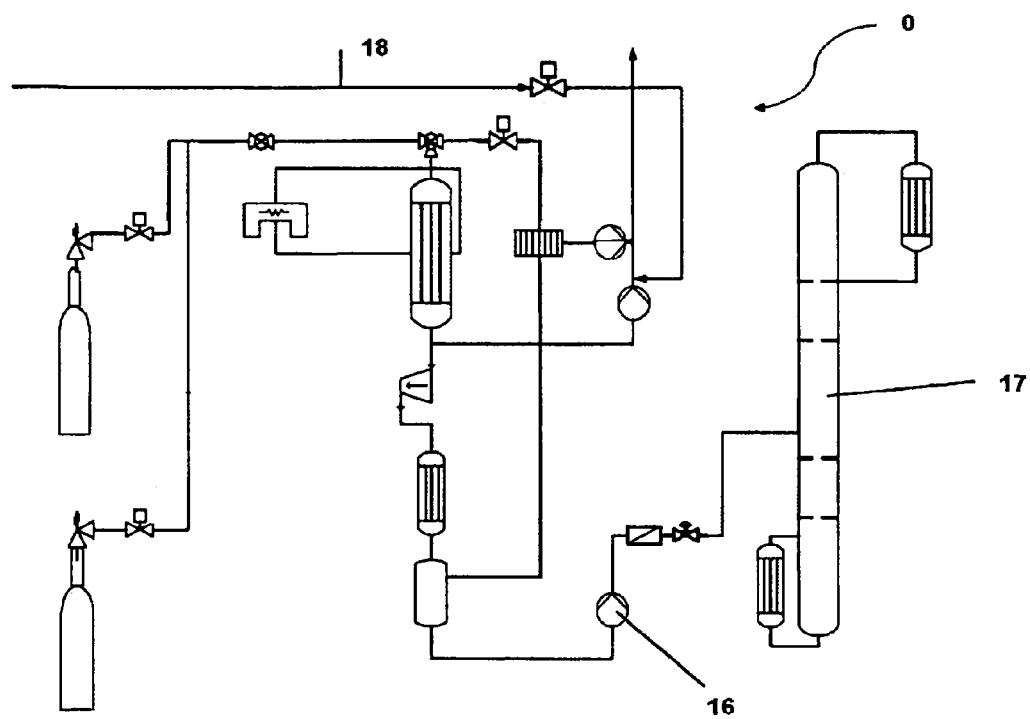
FIG. 2 shows a schematic diagram of a plant 0 with apparatus 17 for separation of the polysilanes, here a distillation column 17.

In a preferred embodiment, which is shown in FIG. 2, the crude product vessel or the crude product outlet is connected to an apparatus 17 for separation of the polysilanes, preferably a column 17 or a multicolumn system 17, more preferably a rectification column, for fractional distillation of the crude product mixture. For complete separation of the polysilanes, a multicolumn system is preferably utilized. If appropriate, the column or multicolumn system may have an upstream product-conveying pump. The low boilers obtained at the top of the column may preferably be ultrahigh-purity tetrasilane, pentasilane and/or hexasilane, and the high boilers obtained at the bottom may be ultrahigh-purity higher molecular weight polysilanes, such as heptasilane, octasilane. For further separation of the silanes, a multicolumn system familiar to those skilled in the art can be used.

A particularly preferred plant 0 has an arrangement of the aforementioned plant parts, in order to enable the performance of a cycle operation of the aforementioned process. In this plant 0, the apparatus 1 comprising at least two reactors 1a has a dedicated downstream compressor 2, as shown in FIG. 1. The apparatus is preferably arranged vertically above the condenser. Said compressor 2 has a dedicated condenser 3, and the plant has the hydrogen-permeable membrane 5 downstream of the condenser 3, with a line 12 dedicated to one side of the membrane 5 and to the reactor 1, and a product outlet 4 or product vessel 4 is also provided downstream of the condenser 3; and discharged hydrogen is removed through a further line 15, which may have a dedicated inert gas line for hydrogen removal, on the other side of the membrane 5.

The example which follows illustrates the process according to the invention in detail.

EXAMPLE 1

Monosilane was vaporized continuously from a pressurized gas bottle 9 by means of a pressure regulator through the reactant feed 12 into the vertical apparatus 1 having series-connected ozonizers 1a and conducted through the gas discharge zones together with dielectric from the ozonizers. The nonthermal plasmas in the ozonizers were operated at minus 10° C. and at 60 $mbar_{abs.}$. The stream of reactants consisted to an extent of 10% by vol. of monosilane and to an extent of 90% by vol. of hydrogen. During the plasma treatment, silyl radicals and higher radicals were formed, which reacted to form polysilanes and formed the resulting phase together with unconverted reactants. The polysilanes, which were liquid under the process conditions, ran off downwards. After increasing the pressure of the resulting phase to around 2.5 $bar_{abs.}$, it was passed through a condenser 3 cooled to about 0° C., in order to completely condense polysilanes formed, which ran off into the crude product vessel 4 which is at a controlled temperature of −40° C. The remaining gaseous resulting phase was run past one side of the membrane 5 through a line 10. Hydrogen in the resulting phase partly diffused through the membrane 5 and was removed via the line 15. At the membrane, a defined ratio of the partial hydrogen pressure to the partial pressure of the monosilane which is gaseous under the conditions selected was set in the resulting phase. As a result of this measure, the resulting phase became a stream of reactants which was fed again to the gas discharge zones comprising dielectric in the ozonizers, after metered addition of further monosilane.

In the crude product vessel, polysilanes were enriched as a mixture having elevated proportions of tetrasilane and pentasilane, which were pumped by the product pump 16 to the distillation column 17, in order to be fractionally distilled therein.

By continuous fractional distillation, ultrahigh-purity tetrasilane is drawn off as a low boiler at the top of the column 17 and pentasilane in a mixture with higher molecular weight polysilanes as a high boiler at the bottom of the column. The pentasilane was obtained in ultrahigh purity at the top of a second column.

The general process regime of Example 1 is not limited to the specified process parameters, but can be generalized in accordance with the description.

LIST OF REFERENCE NUMERALS

0 plant
1 apparatus comprising at least two reactors
1a reactor(s), ozonizer(s)
2 compressor
3 condenser
4 crude product outlet or crude product vessel
5 membrane
6 vacuum pump
7 inverter for plasma production
8 hydrogen source—startup of the process
9 monosilane source
10 line/resulting phase
11 line/reactant feed
12 line/reactant feed 13 line/monosilane
14 line/resulting phase
15 line/hydrogen
16 product-conveying pump
17 apparatus for separation of polysilanes (column—fractional distillation)
18 line—inert gas for hydrogen removal

The invention claimed is:

1. A process for preparing a polysilane, comprising:

subjecting a stream of reactants comprising monosilane of the formula (I) and hydrogen to at least one gas discharge such that a resulting phase comprising a polysilane is produced;

condensing the resulting phase, 4 such that a liquid phase comprising the polysilane and a gas phase comprising hydrogen and gaseous silanes are formed from the resulting phase, wherein the gaseous silanes in the gas phase comprise unconverted monosilane;

setting a ratio of a partial pressure of the hydrogen to a partial pressure of the gaseous silanes in the gas phase to be a predetermined ratio; and separating the polysilane in the liquid phase obtained in the condensing, wherein the polysilane has at least two silicon atoms bonded to one another via a covalent single bond, and comprises at least one selected from the group consisting of linear, branched, or cyclic tetrasilane, linear, branched, or cyclic pentasilane, and linear, branched, or cyclic hexasilane.

2. The process according to claim 1, wherein each of the condensing of the resulting phase and the setting of the ratio is conducted under a pressure higher than a pressure under which the stream is subjected to the gas discharge.

3. The process according to claim 1,
wherein the hydrogen, after the ratio of the partial pressure of the hydrogen to the partial pressure of the gaseous silanes in the gas phase is set to be the predetermined ratio, the gas phase has a pressure of 1 $bar_{abs}$ to 100 $bar_{abs}$.

4. The process according to claim 1, wherein the monosilane is subjected to the gas discharge in the presence of the hydrogen at a pressure of 0.05 $mbar_{abs}$ to 15,000 $mbar_{abs}$.

5. The process according to claim 1, wherein the polysilane comprises linear, branched, or cyclic tetrasilane and linear, branched, or cyclic pentasilane.

6. The process according to claim 1, wherein the stream of reactants is subjected to two to ten gas discharges.

7. The process according to claim 1, wherein the gas discharge is effected within a temperature range of from −60° C. to 10° C.

8. The process according to claim 1, wherein a ratio in per cent by volume (% by vol.) of the hydrogen to the monosilane in the stream of reactants is from 15:1 to 1:5.

9. The process according to claim 1, wherein, in the subjecting, the stream of reactants is subjected to at least one nonthermal plasma.

10. The process according to claim 1, wherein the separating of the polysilane is conducted by at least one of distillation, fractional condensation, and chromatography.

11. The process according to claim 1, wherein the setting of the ratio is performed by a hydrogen-permeable membrane.

12. The process according to claim 11, wherein the membrane is permeable to hydrogen and essentially impermeable to the monosilane and the polysilane.

13. The process according to claim 1, wherein the monosilane is subjected to the gas discharge in the presence of the hydrogen at a pressure of 0.1 $mbar_{abs}$ to 1,000 $mbar_{abs}$.

14. The process according to claim 1, wherein, in the subjecting, the stream of reactants is subjected to at least one nonthermal plasma at a temperature range of from −40° C. to 0° C.

15. The process according to claim 14, wherein the stream of reactants is subjected to two to four nonthermal plasmas.

16. The process according to claim 1, wherein, in the subjecting, the stream of reactants is subjected to at least one nonthermal plasma at a temperature of −10±5° C.

* * * * *